(12) United States Patent
Kincaid

(10) Patent No.: US 6,950,756 B2
(45) Date of Patent: Sep. 27, 2005

(54) REARRANGEMENT OF MICROARRAY SCAN IMAGES TO FORM VIRTUAL ARRAYS

(75) Inventor: Robert Kincaid, Half Moon Bay, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 108 days.

(21) Appl. No.: 10/359,454

(22) Filed: Feb. 5, 2003

(65) Prior Publication Data

US 2004/0153251 A1 Aug. 5, 2004

(51) Int. Cl.⁷ ................................................. G06F 17/00
(52) U.S. Cl. ................................. 702/19; 702/20; 435/6
(58) Field of Search .......................... 702/19, 20; 435/6

(56) References Cited

FOREIGN PATENT DOCUMENTS

WO    WO-01/27809 A2 *   4/2001

* cited by examiner

Primary Examiner—James Martinell

(57) ABSTRACT

A system and methods for selecting single-features from a microarray scan image of genomic data and rearranging the selected single-features of the microarray into a virtual array having a format or arrangement that is more relevant or informative to the analyst or user than that of the original microarray scan image.

29 Claims, 6 Drawing Sheets

REARRANGEMENT OF MICROARRAY SCAN IMAGES TO FORM VIRTUAL ARRAYS

FIELD OF THE INVENTION

The present invention pertains to software systems which divide a microarray scan image into feature cells and then recombines those cells into a new virtual array image that provides only feature cells which are relevant and appropriate to the subject analysis, thus providing for easier visualization and more meaningful data extraction and management.

BACKGROUND OF THE INVENTION

Pharmaceutical, biotechnology, or genomics companies use polynucleotide arrays (such as DNA or RNA arrays), for example, as diagnostic or screening tools. Such arrays or microarrays include regions (sometimes referenced as spots or features) of usually different sequence polynucleotides arranged in a predetermined configuration on a substrate such as a microchip. The arrays, when exposed to a sample, will exhibit a binding pattern. This binding pattern can be observed, for example, by labeling all polynucleotide targets (for example, DNA) in the sample with a suitable label (such as a fluorescent compound), and accurately observing the fluorescent signal on the array. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated using either in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). The deposition methods basically involve depositing biopolymers at predetermined locations on a substrate which are suitably activated such that the biopolymers can link thereto. Biopolymers of different sequence may be deposited at different regions of the substrate to yield the completed array. Washing or other additional steps may also be used. Procedures known in the art for deposition of polynucleotides, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of an ink jet type head to fire drops onto the substrate).

A scanner is then used to read the fluorescence of these resultant surface bound molecules under illumination with suitable (most often laser) light. The scanner acts like a large field fluorescence microscope in which the fluorescent pattern caused by binding of labeled molecules is scanned on the chip. In particular, a laser induced fluorescence scanner provides for analyzing large numbers of different target molecules of interest, e.g., genes/mutations/alleles, in a biological sample.

The scanning equipment typically used for the evaluation of microarrays includes a scanning fluorometer. A number of different types of such devices are commercially available from different sources, such as Axon Instruments in Union City, Calif. and Perkin Elmer of Wellesly, Mass. Analysis of the data, (i.e., collection, reconstruction of image, comparison and interpretation of data) is performed with associated computer systems and commercially available software, such as GenePix by Axon Instruments, QuantArray by Perkin Elmer or Feature Extraction by Agilent of Palo Alto, Calif.

In such scanning devices, a laser light source generates a—most often collimated—beam. The collimated beam sequentially illuminates small surface regions of known location on an array substrate. The resulting fluorescence signals from the surface regions are collected either confocally (employing the same lens used to focus the laser light onto the array) and/or off-axis (using a separate lens positioned to one side of the lens used to focus the laser onto the array). The collected signals are then transmitted through appropriate spectral filters to an optical detector. A recording device, such as a computer memory, records the detected signals and builds up a raster scan file of intensities as a function of position, or time as it relates to the position. Such intensities, as a function of position, are typically referred to in the art as "pixels" or "pixel values." Collectively, the pixels make up a microarray scan image having a multiplicity of feature cells, wherein each feature cell is comprised of a group of pixels.

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced spots.

The use of microarray technologies to conduct experiments that measure thousands of genes and proteins simultaneously and under different conditions are becoming the norm in both academia and pharmaceutical/biotech companies. Microarray technology is leading to greater feature density as well as to extremely high-resolution scanning. In their largest capacities, such as in a full human genome catalog array, there may be as many as three or four 25,000 to 50,000-feature cells. This results in increasingly large amounts of both image and feature analysis data which can be problematic for several reasons. First and foremost, many, if not most, features on a typical catalog array may be inconsequential to the experiment being conducted. Secondly, the high density and large number of features on an array make it difficult or impossible to do effective visual feature-to-feature comparisons. Additionally, the more features and the greater complexity of an array, the more difficult it is to create a logical layout of probes that is meaningful to the experimenter. This is particularly problematic for catalog arrays, where the nature and purpose of the experiment may be unknown at the time of the array design.

While advancements in bioinformatics have been made which help scientists to extract, build and verify interpretations and hypotheses about microarray data, all of the features of the array must first be extracted before the results can be streamlined. There is still a need to further streamline the data in order to minimize the volume of data to only that which is particularly relevant to the hypothesis or experiment at hand and to facilitate the visualization of high-density arrays. The present invention seeks to provide such streamlining of data prior to extraction of the features from the array in order to reduce to the volume of data being produced as well as to facilitate visualization and inspection of high-density arrays.

SUMMARY OF THE INVENTION

The present invention provides a system and methods for selecting single-features from a microarray scan image of genomic data and rearranging the selected single-features or image cells into a format or arrangement that is more relevant or informative to the analyst or user. Such resulting arrangement is also in the form of a microarray image, referred to as a "virtual" image array. All or less than all of the single-features of a microarray may be selected for rearrangement into one or more virtual arrays. In essence, a virtual array may provide for any number of single-features rearranged or reorganized in any logical or relevant permutation.

The system of the present invention includes a computer readable medium carrying one or more sequences of instructions from a user of a computer system for converting an original microarray scan image into a virtual array image of selected features from the original array in a selected arrangement and optionally visually presenting the rearranged virtual array image, wherein the execution of the one or more sequences of instructions by one or more processors cause the one or more processors to perform the steps of accessing one or more original microarray scan images, selecting relevant feature cells, singulating the selected feature cells from the original microarray scan image by cropping them out of the full scan image and rearranging the singulated, selected feature cells into a virtual array image. The virtual array image may then be processed as would the original microarray scan image by the same standard image processing and data extraction tools, as are typically used in microarray analysis. These tools may involve further image cropping, feature location, compilation of feature pixel statistics, various data normalization schemes, systematic error corrections, etc. For example, the same feature extraction software which is routinely used on the original microarray scan may also be used to extract data from the virtual array. The subject methods may also include creating a reordered subset of the original microarray design file to reflect each of the feature locations on the new virtual image in order to convey such location information to the feature extraction software.

Among other advantages, the present invention reduces the data handling and computation requirements particularly for those virtual arrays representing a relatively small percentage of the features of the original array.

The present invention also makes human inspection of array images more approachable and manageable by allowing only selected or relevant features to be visualized together in an arrangement that maximizes the usefulness of the resulting data.

Additionally, the present invention makes it possible to visualize features in a variety of virtual arrangements which may help to elucidate previously unknown trends and relationships amongst the features.

Another advantage of the present invention is that it provides a means for publishing only those features of a microarray scan image and corresponding extracted data which are desired without having to publish other features containing proprietary data. For example, where patient privacy is an issue, only probes relevant to a particular diagnosis may be made available where information about other probes is not published.

A feature of the present invention is that the synthetic features having fixed values or previously processed real features having known values may be used to validate the feature extraction software being used.

These and other objects, advantages, and features of the invention will become apparent to those persons skilled in the art upon reading the details of the invention as more fully described below.

BRIEF DESCRIPTION OF THE DRAWINGS

Each of the figures diagrammatically illustrates aspects of the invention.

DEFINITIONS

Figure 1:
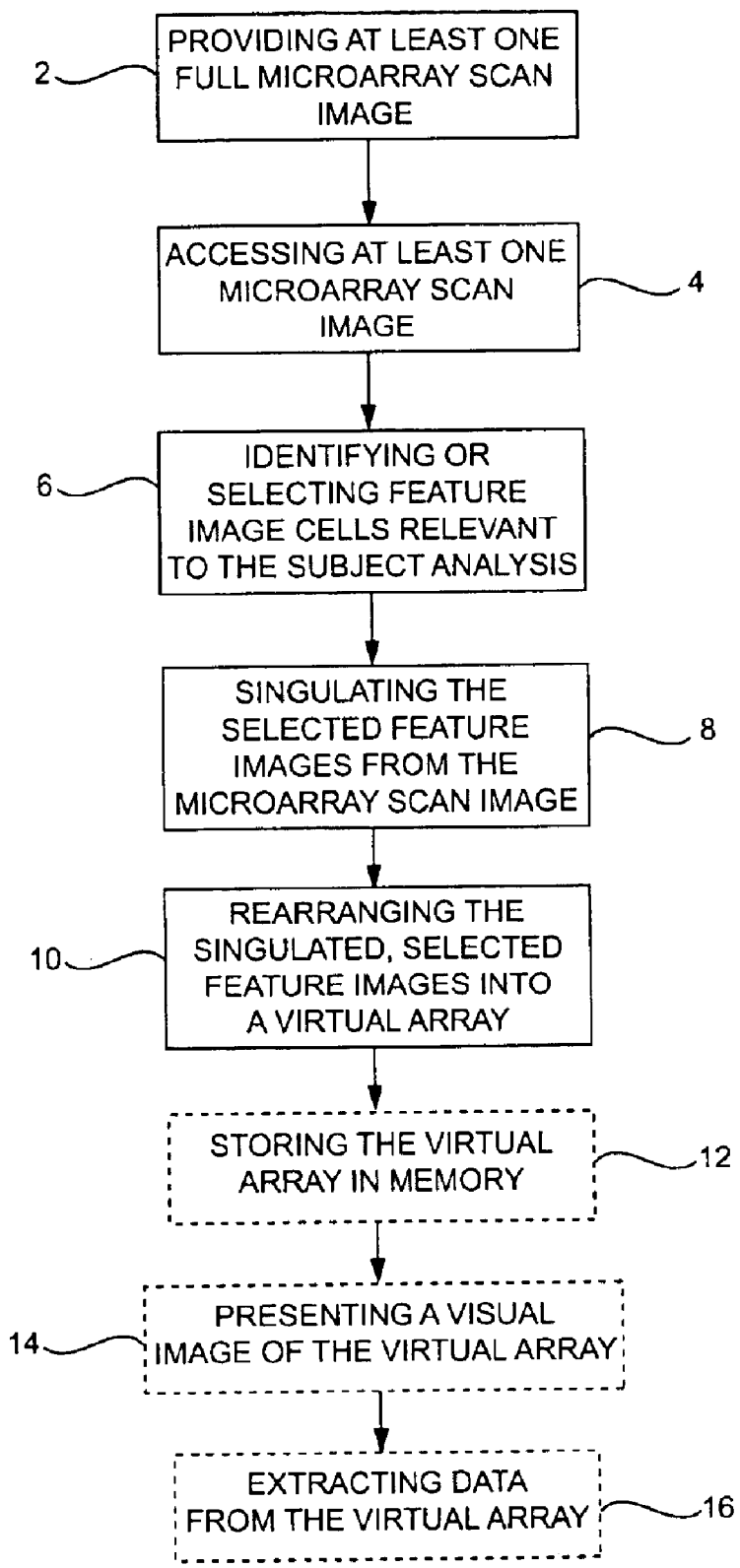
FIG. 1 is a flow chart illustrating one method of the present invention by which at least one microarray scan image is rearranged into a virtual array having an arrangement of selected features which is more relevant, easily managed and readily visualized.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer/polymer) of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array" or "microarray," includes any two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand, more ten thousand features, or even more than one hundred thousand features, in an area of less than 20 cm² or even less than 10 cm². For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each microarray may cover an area of less than 100 cm², or even less than 50 cm², 10 cm² or 1 cm². In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Microarrays can be fabricated using drop deposition from pulsed jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other).

A "scan region" refers to a contiguous (e.g., rectangular) area in which the array spots or features of interest, as defined above, are found. The scan region is that portion of the total area illuminated from which the resulting fluorescence, chemiluminescence, or other optical detection techniques is detected and recorded. For the purposes of this invention, the scan region includes the entire area of the slide scanned in each pass of the lens, between the first feature of interest, and the last feature of interest, even if there exist intervening areas that lack features of interest. The scan region does not, however, include "border regions" or "borders" of the array substrate/slide adjacent slide edges and adjacent to but not including or covered by array features. Generally, any borders around the scan region are less than about 5–15 mm and can be as little as 1 mm, or even smaller, if the mechanical design of the slide holder permits it. It is often desirable to lay down features as close to the edge of the substrate as possible so as to maximize the number of different probes that may be displayed on a given surface area. As such, in many array configurations, the width of a border, if present, between the scanned arrays and the slide edge does not exceed about 20 mm, usually does not exceed about 10 mm and more usually does not exceed about 5 mm.

An "array layout" refers to one or more characteristics of the features, such as feature positioning on the substrate, one or more feature dimensions, and an indication of a moiety at a given location.

"Hybridizing" and "binding", with respect to polynucleotides, are used interchangeably.

A "computer-based system" or "computer system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF PREFERRED EMBODIMENTS

Before the present system, tools and methods are described, it is to be understood that this invention is not limited to particular data sets, commands or steps described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a step" includes a plurality of such steps and reference to "the feature" includes reference to one or more features and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided might be different from the actual publication dates which may need to be independently confirmed.

The present invention provides a system and methods for selecting single-features from a microarray scan image of genomic data and rearranging the selected single-features or image cells into a format or arrangement that is more relevant or informative to the analyst or user. Such resulting arrangement is also in the form of a microarray image, referred to as a "virtual" array or virtual microarray. All or less than all of the single-features of a microarray may be selected for rearrangement into one or more virtual arrays. In essence, a virtual array may provide for any number of single-features rearranged or reorganized in any logical or relevant permutation.

Examples of such permutations are as follows. In one embodiment or variation of the present invention, all of the features of a microarray are included but are rearranged to place related probes next to each other. For example, all probes showing up-regulation may be placed adjacent to each other and all probes showing down-regulation may be placed adjacent to each other. The probes may be further sorted in order of intensity. Additionally, probes which are known to be problematiccan be selectively eliminated from the virtual array. For example, analysis of pixel statistics about a given feature can often predict if a feature is flawed or damaged in some way. These error statistics can be used to ignore entirely such flawed or damaged features so that they are not part of the virtual array image. Additionally, pixel statistics of the surrounding background can often indicate if there is a manufacturing or processing issue with that region of the microarray. These areas could also be excluded in the virtual array image.

In another embodiment or variation of the present invention, a microarray may be reorganized into one or more much smaller virtual arrays where each virtual array provides a subset of feature-specific images or images having statistically appropriate features which are highly suitable for normalization. For example, a full human genome catalog array could be reduced through image processing to appear as one or more much smaller arrays having features specific only to genes related to a particular diagnosis, such as predictors for heart disease, diabetes, various cancers, etc. Each of these smaller virtual arrays could be specific to an individual diagnosis. As stated earlier, by excluding those probes related to other potential diagnostics, the patient's privacy is protected. More generally a virtual array might be constructed for a specific scientific measurement, e.g., pathway analysis, metabolism, etc. For example, a generic human genome catalog array could be rearranged into several smaller virtual arrays relevant to specific biological pathways. Those features representing proteins involved in a particular metabolic or signaling pathway could be isolated to a single virtual array for a specific analysis. A virtual array relevant to the MAPK signaling pathway might be constructed from a more extensive and generic catalog array. As such, a 25,000 to 50,000-feature array may be paired down to a 1,000-feature array or several 1,000-feature arrays which are much easier to manage and visualize by the analyst.

In still another variation or embodiment of the present invention, two or more or a set of microarrays may be reduced to a single array providing a combined subset of features from each of the microarrays. For example, at current array densities, a human genome catalog set might take three or four 25,000-feature arrays. If the analyst is interested in, for example, only genes related to angiogenesis, only features relevant to such genes are selected from each of the arrays and recombined into a single virtual array. Such an embodiment is ideally suited for cluster analysis or the like where the array analysis system is not designed to properly handle multi-array sets.

Another aspect of the present invention is that artificial features may be introduced into the virtual array and commingled with real features from the original microarray. The artificial features represent synthetic data which have known values, e.g., raw signal, ratio, statistics, etc., which produce known feature extraction results. The known synthetic data points can be used to validate whether or not the analysis software is performing correctly during manual or automated feature extraction. The synthetic data need not be completely contrived but may be previously extracted data from real features which are used as reference points when testing the software.

This software validation technique may also be applied to full scan images by simply overlaying a row or column of synthetic feature images over a corresponding row or column of original features. A variation of this technique involves adding the new synthetic features to new and unused feature locations of the original microarray scan. As such, the newly constructed image may actually be larger than the original scan.

Referring to FIG. 1, one general method according to the present invention is shown in flow chart form. Initially at step 2, at least one full microarray scan image is provided in a computer-readable form which is accessible by a computer system. Any number of microarray scan images may be provided including an entire human genome catalog. Next at 4, the at least one microarray scan image is then accessed by a means for accessing the microarray image of the system according to an instruction by the user of the computer system. The user, at step 6, then identifies or selects feature cells which he or she desires to have displayed in the virtual array. This selection may be based on any number of factors such as by related probes, probe intensity, one or more gene specific features, etc. The features are selected by a means for selecting features of the system according to an instruction by the user.

The selection process may be automated by providing a pre-existing virtual design file that specifies which features are to be selected for inclusion into the virtual array. The virtual design file may be created by manipulating the original design file to include only probes desired by the user. Alternatively, the selection process may be statistically based by selecting only those features having a low error estimates (indicating high confidence in the measurement). Still yet, selection may be based on selecting only those features having a probe intensity level above a selected threshold level. For assays involving two color signals, the features may be selected up-to-down regulation ration is greater than 2, for example. Feature selection may also be done by the user manually.

With any of the above feature selection methods, the selected features are then singulated from the full microarray scan image by "cropping" each selected feature from the full microarray in step 8 by a means for singulating the microarray. The selected features are located with the individual pixels representing each selected feature's image cell then being copied into a corresponding area of the virtual array image defined by the virtual array design file. The singulated, selected features are then rearranged into a virtual array format in step 10 by a means for rearranging the features.

Once the virtual array is completely assembled, various optional steps may be taken. The virtual array may be stored in a database (step 12) and cross-referenced in the database by whatever features or parameters make sense for later access and retrieval by researchers and other users. By saving the much smaller virtual arrays rather than the original full-scale microarray scans, computer memory is optimally used. Additionally, much time can be saved when processing and retrieving data from the virtual arrays which have been stored in memory.

The virtual array may also be visually illustrated (step 14) on a monitor or otherwise printed out by means for visualizing the virtual array. Based upon an instruction initiated by the user, the data may then be extracted from the virtual array in a conventional manner (step 16) by a means for extracting data.

Figure 2:
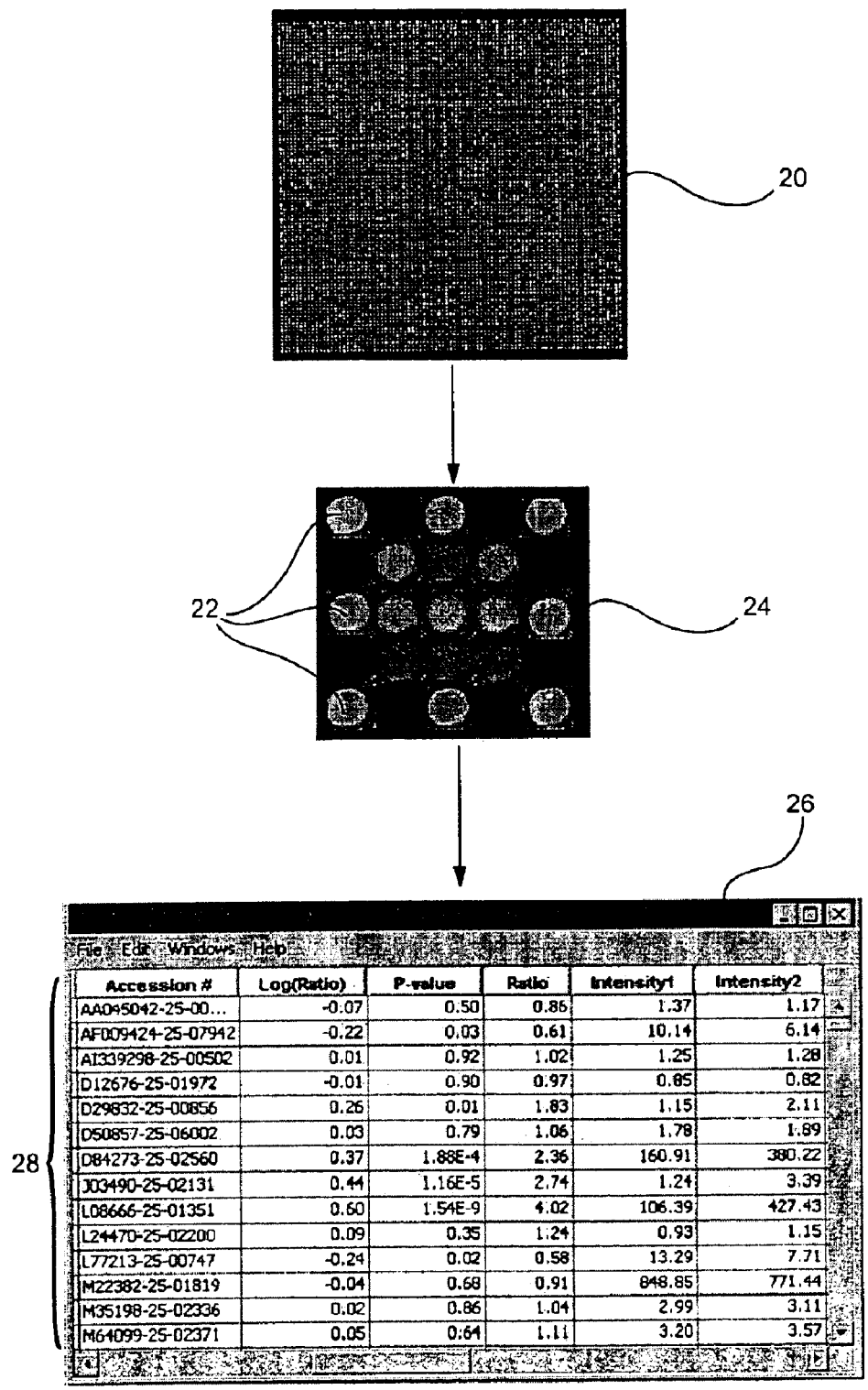
FIG. 2 is a diagram illustrating various steps of one variation of the method of FIG. 1 wherein selected features of a single microarray are rearranged into a smaller virtual array.
Figure 3:
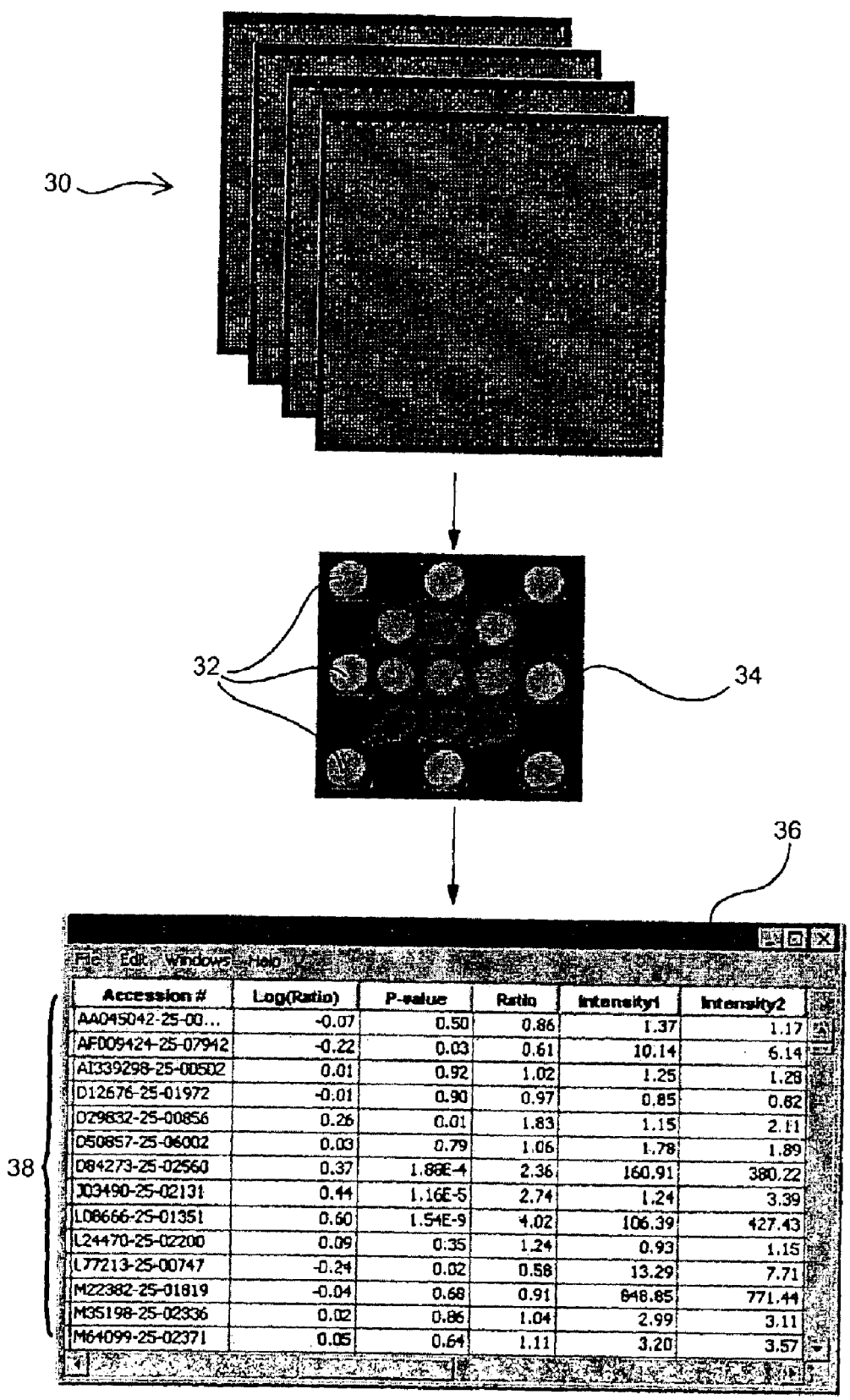
FIG. 3 is a diagram illustrating various steps of another variation of the method of FIG. 1 wherein selected features of multiple microarrays are rearranged into a smaller, single virtual array.
Figure 4:
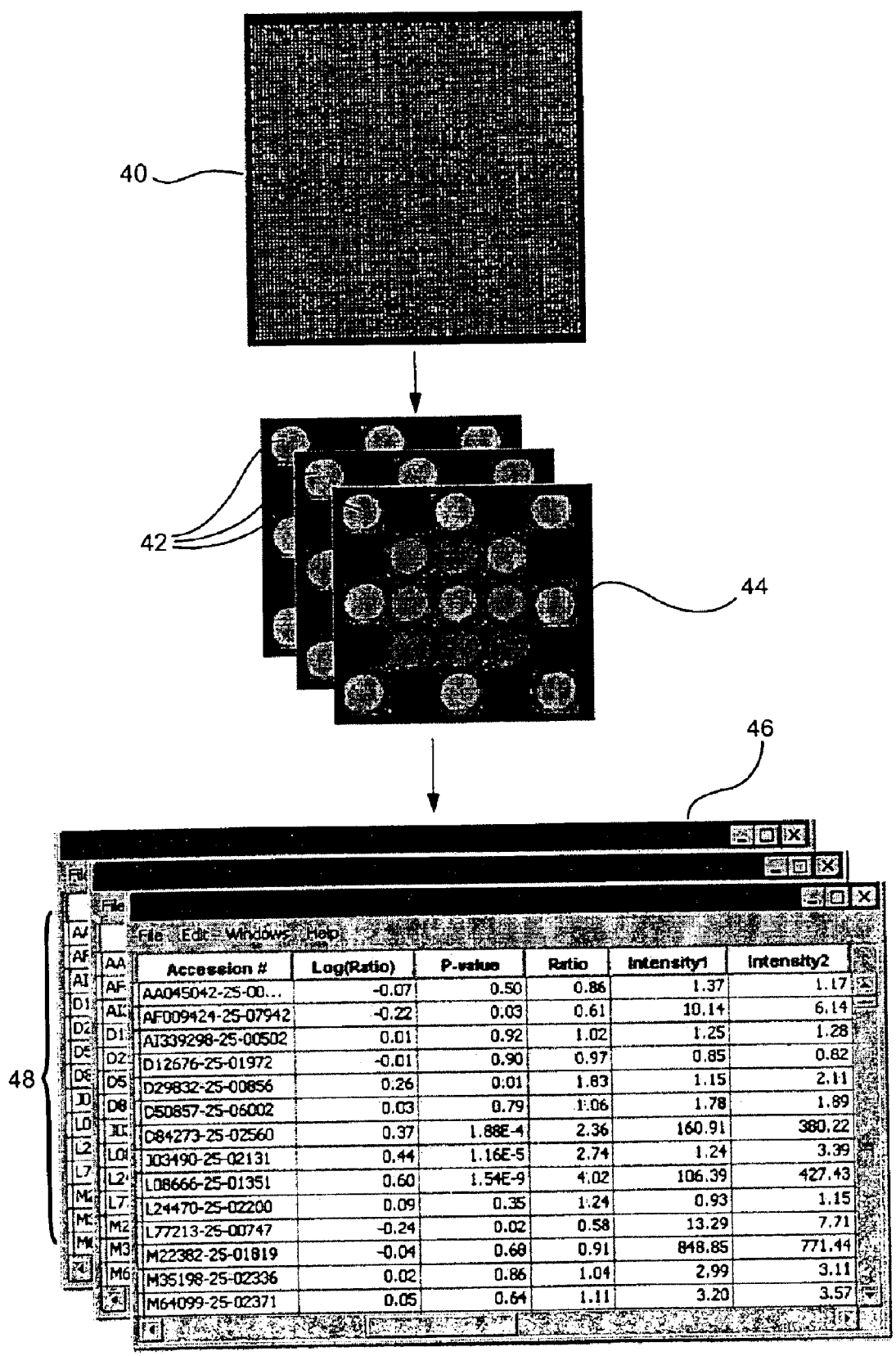
FIG. 4 is a diagram illustrating various steps of another variation of the method of FIG. 1 wherein selected features of a single microarray are rearranged into various smaller virtual arrays containing logically organized subsets of those selected features.

FIGS. 2, 3 and 4 illustrate several applications of the above-described method. In FIG. 2, a full microarray scan image 20, such as a human genome catalog comprising 50,000-features, is provided. From microarray 20, a user selects individual features 22 which are then singulated from microarray 20 and rearranged into virtual array 24 in a selected arrangement. By means of data extraction software algorithms, such as those disclosed in commonly assigned European Patent Application EP 1162572 A2, herein incorporated by reference in its entirety, raw data 28 is extracted from each of the selected features 22 and displayed in a human-readable format 26.

In FIG. 3, a set of microarray scan images 30 is provided. From microarray set 30, a user selects individual features 32 which are then singulated from each of the microarrays of microarray set 30. The singulated, selected features 32 are then rearranged into a virtual array 34. By means of data extraction software algorithms, raw data 38 is extracted from each of the selected features 32 and displayed in a human-readable format 36.

In FIG. 4, a microarray scan image 40 is provided. From microarray 40, a user selects individual features 42 which are then singulated from microarray 40. The singulated, selected features 42 are then rearranged into a set of virtual arrays 44 wherein each virtual array contains related features 42. By means of data extraction software algorithms, raw data 48 is extracted from each of the selected features 42 for each of the virtual arrays 44 and displayed in a human-readable format 46.

Figure 5:
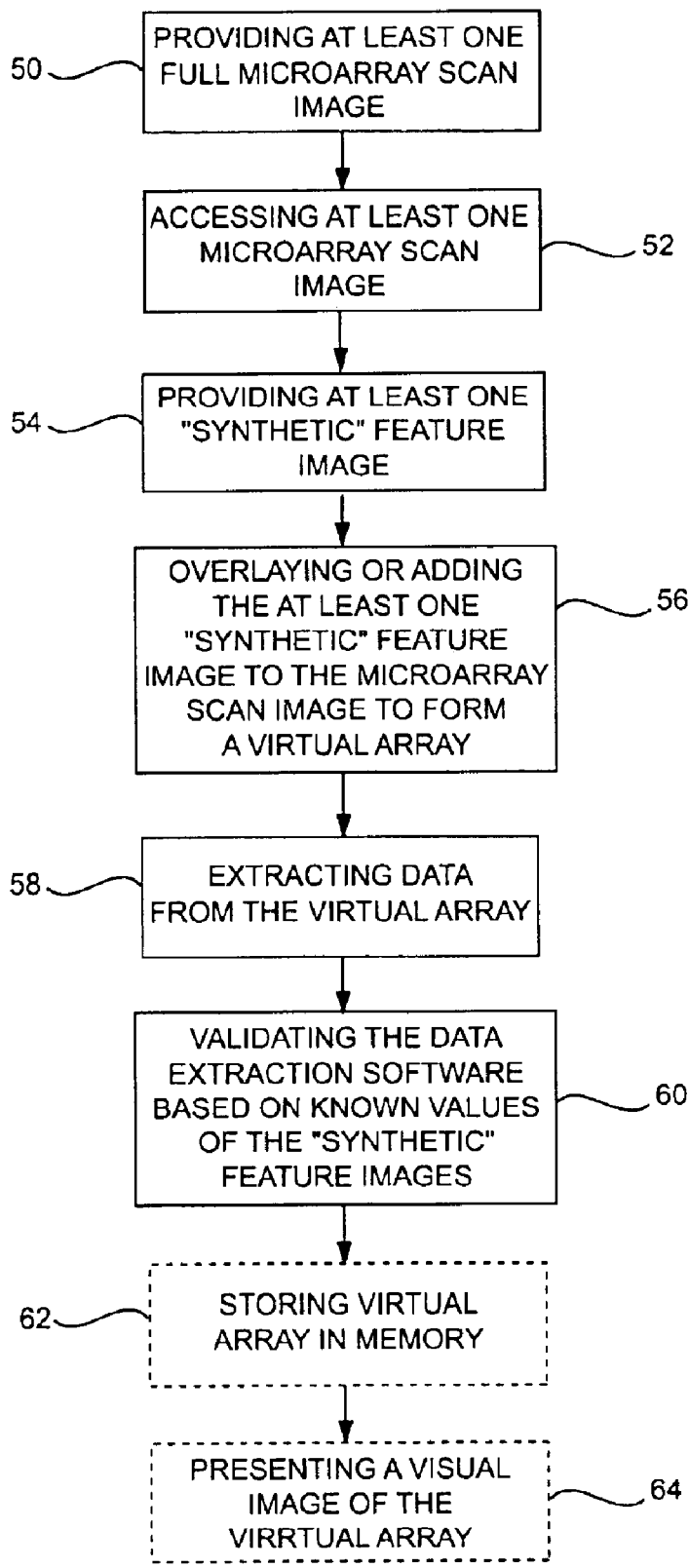
FIG. 5 is a flow chart illustrating another method of the present invention by which at least one microarray scan image is rearranged into a virtual image containing at least one synthetic feature which is used to validate data extraction software.

Another method of the present invention involving the formation of a virtual array is illustrated in the flow chart of FIG. 5. Initially at step 50, at least one full microarray scan image is provided in a computer-readable form which is accessible by a computer system. Any number of microarray scan images may be provided including an entire human genome catalog. Next at step 52, the at least one microarray scan image is then accessed by a means for accessing the microarray image of the system according to an instruction by the user of the computer system. By an instruction from the user to the means for providing "synthetic" feature, at least one synthetic feature is provided (step 54), and then by means of overlaying or adding a synthetic feature having known raw data values, such synthetic feature is overlaid or added to the micro array scan image to form a virtual array (step 56). Then, based upon an instruction initiated by the user, the data may then be extracted from the virtual array in a conventional manner by a means for extracting data (step 58). By software instruction means for validating the extraction means, the extracted data is evaluated compared to the known data values to determine whether the extraction software is functioning properly (step 60).

Other additional optional steps may also be taken. The virtual array may be stored in a database (step 62) and cross-referenced in the database according to the synthetic features for later access and retrieval by researchers and other users. The virtual array may also be visually illustrated on a monitor or otherwise printed out by means for visualizing the virtual array (step 64).

Figure 6:
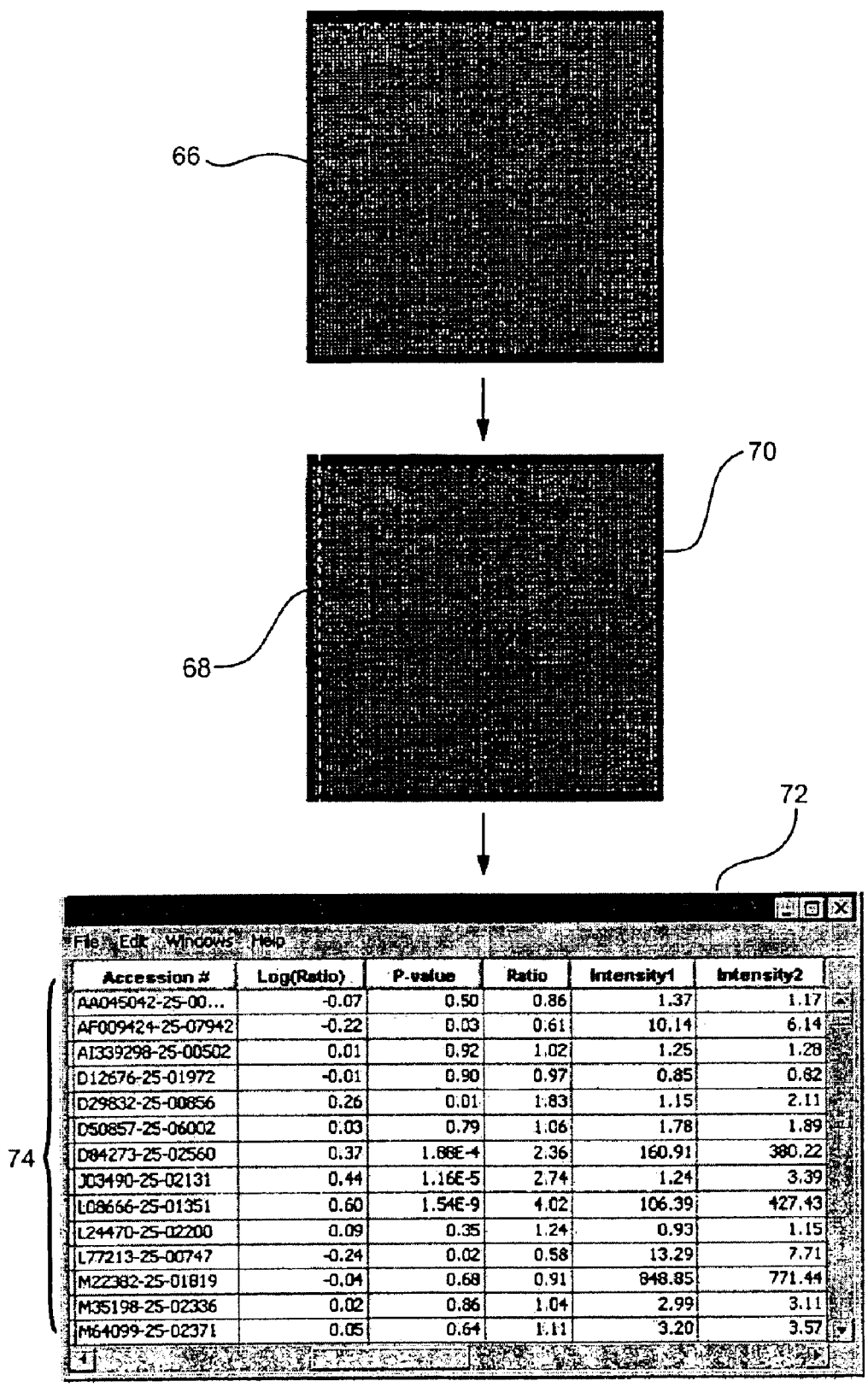
FIG. 6 is a diagram illustrating various steps of one variation of the method of FIG. 5 wherein a column of features of a microarray has been overlayed with synthetic column of features having fixed data values.

FIG. 6 illustrates an application of the above-described validation method. A full microarray scan image 66 is provided. An artificial column 68 of features is selectively overlayed or added to microarray 66 to form a virtual array 72. By means of data extraction software algorithms, raw data 74 is extracted from at least the overlayed or added features 68 of virtual array 70 and is displayed in a human-readable format 72. The user may then automatically or visually compare the extracted data to the known values of the raw data of features 68 to determine whether the extraction software is functioning properly. If the extracted values are found to be the same as the known values, the software is working properly.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, data type, network, user need, process, process step or steps, to the objective, spirit and scope of the present invention. All such modifications are intended to be within the scope of the claims appended hereto.

That which is claimed is:

1. A method of creating at least one virtual microarray scan image using at least one real microarray scan image, the method comprising:

providing at least one microarray scan image having an array of feature images;

accessing said at least one microarray scan image;

selecting feature images from said at least one real array of feature images;

singulating said selected feature images from said at least one real microarray scan image; and rearranging said singulated feature images into at least one virtual microarray.

2. The method of claim 1, further comprising storing said at least one virtual microarray.

3. The method of claim 1, further comprising said presenting a visual image of said at least one virtual microarray for a user to visualize.

4. The method of claim 1, further comprising extracting data from at least one of said features in said at least one virtual microarray.

5. The method of claim 4, further comprising publishing said extracted data from said at least one virtual microarray.

6. The method of claim 1, wherein said singulating comprises cropping said selected feature images from said at least one microarray scan image.

7. The method of claim 1, wherein said selecting feature images comprises selecting features from two or more real microarray images.

8. The method of claim 7, wherein said rearranging said singulated feature images comprises rearranging said singulated feature images into two or more virtual arrays.

9. The method of claim 1, wherein said selecting feature images comprises selecting feature images which have probes which are up-regulated.

10. The method of claim 1, wherein said selecting feature images comprises selecting feature images which have probes which are down-regulated.

11. The method of claim 9 or 10 wherein said rearranging said singulated feature images comprises rearranging said feature images according to probe intensity.

12. The method of claim 1 wherein said selecting feature images comprises selecting feature images relevant to a specific medical diagnosis.

13. The method of claim 1 wherein said selecting feature images comprises selecting feature images relevant to a specific scientific measurement.

14. A method of creating at least one virtual microarray scan image using at least one real microarray scan image, the method comprising:

providing at least one real microarray scan image having an array of feature images;

accessing said at least one real microarray scan image;

providing at least one synthetic feature; and overlaying or adding said at least one synthetic feature image to the real microarray scan image to form at least one virtual microarray.

15. The method of claim 14, further comprising extracting data from said at least one virtual microarray.

16. The method of claim 15, wherein said extracting data is performed using data extraction software.

17. The method of claim 16, further comprising validating said data extraction software used to perform said extracting.

18. The method of claim 14, further comprising storing said at least one virtual microarray.

19. The method of claim 14, further comprising presenting a visual image of said at least one virtual microarray for a user to visualize.

20. A computer readable medium carrying one or more sequences of instructions from a user of a computer system for creating at least one virtual microarray scan image using at least one real microarray scan image, wherein the execution of the one or more sequences of instructions by one or more processors cause the one or more processors to perform the steps of:

providing at least one real microarray scan image having an array of feature images;

accessing said at least one real microarray scan image;

selecting feature images of said at least one real microarray scan image;

singulating said selected feature images from said at least one real microarray scan image; and rearranging said singulated feature images into at least one virtual microarray.

21. The computer readable medium of claim 20, wherein the following further step is performed:

storing said at least one virtual microarray in memory.

22. The computer readable medium of claim 20, wherein the following further step is performed:

presenting a visual image of said at least one virtual microarray for a user to visualize.

23. The computer readable medium of claim 20 wherein the following further step is performed:

extracting data from said at least one virtual array.

24. The computer readable medium of claim 20, wherein the following further step is performed:

publishing said extracted data from said at least one virtual array.

25. A computer readable medium carrying one or more sequences of instructions from a user of a computer system for creating at least one virtual microarray scan image using at least one real microarray scan image, wherein the execution of the one or more sequences of instructions by one or more processors cause the one or more processors to perform the steps of:

providing at least one real microarray scan image having an array of feature images;

accessing said at least one real microarray scan image;

providing at least one synthetic feature; and overlaying or adding said at least one synthetic feature to said real microarray scan image to form at least one virtual microarray.

26. The computer readable medium of claim 25, wherein the following further step is performed:

extracting data from said at least one virtual microarray.

27. The computer readable medium of claim 26, wherein the following further step is performed:

validating the data extraction software used to perform said step of extracting.

28. The computer readable medium of claim 25, wherein the following further step is performed:

storing said at least one virtual microarray in memory.

29. The computer readable medium of claim 25, wherein the following further step is performed:

presenting a visual image of said at least one virtual microarray for a user to visualize.

* * * * *